(12) United States Patent
Haindl

(10) Patent No.: US 7,115,111 B2
(45) Date of Patent: *Oct. 3, 2006

(54) CANNULA SYSTEM

(75) Inventor: Hans Haindl, Wennigsen (DE)

(73) Assignee: Disetronic Licensing AG, Burgdorf (CH)

( * ) Notice: Subject to any disclaimer, the term of this patent is extended or adjusted under 35 U.S.C. 154(b) by 539 days.

This patent is subject to a terminal disclaimer.

(21) Appl. No.: 10/309,082

(22) Filed: Dec. 4, 2002

(65) Prior Publication Data

US 2003/0073957 A1 Apr. 17, 2003

Related U.S. Application Data

(63) Continuation of application No. 09/446,066, filed as application No. PCT/EP98/03620 on Jun. 16, 1998, now Pat. No. 6,537,253.

(30) Foreign Application Priority Data

Jun. 18, 1997 (DE) ................................ 197 25 680

(51) Int. Cl.
*A61M 5/178* (2006.01)

(52) U.S. Cl. ................................ 604/158; 604/164.01

(58) Field of Classification Search ................ 604/158, 604/159, 160, 161, 162, 164.01, 164.02, 604/164.08, 164.09, 164.07; 606/108

See application file for complete search history.

(56) References Cited

U.S. PATENT DOCUMENTS

| 1,527,291 A | 2/1925 | Zorraquin |
| 3,682,173 A | 8/1972 | Center |
| 4,869,717 A | 9/1989 | Adair |
| 5,129,884 A | 7/1992 | Dysarz |
| 5,441,481 A | 8/1995 | Mishra et al. |
| 5,573,510 A | 11/1996 | Isaacson |
| 5,575,777 A | 11/1996 | Cover et al. |
| 6,537,253 B1 * | 3/2003 | Haindl ........................ 604/158 |

FOREIGN PATENT DOCUMENTS

| DE | 23 05 640 | 8/1975 |
| DE | 31 47 609 | 6/1983 |
| DE | 33 41 170 | 5/1984 |
| DE | 3342170 | 8/1995 |
| DE | 197 14 572 | 6/1998 |

(Continued)

*Primary Examiner*—Manuel Mendez
(74) *Attorney, Agent, or Firm*—Shlesinger, Arkwright & Garvey LLP

(57) ABSTRACT

A cannula system (1) comprising a tubular housing (7) having a front and a rear end. A slider (6) is displaceably mounted inside the housing (7) between a front and a rear limit position. A tear end (5) of a cannula (3) is rigidly joined to the slider (6), the front end of said cannula being fitted with a front end (4) having a tip to pierce biological tissue and extending into the front end of the housing (7) when the slider (6) is in the rear limit position. Means are provided to move the cannula (3) back. A catheter (2) is affixed to the rear end of the housing (7) in the direction opposite the direction of piercing and extends at least in part through the slider (6) and into the cannula (3), preferably as far as the front end of said cannula, when the slider (6) is in its front limit position and the cannula (3) projects from the front end of the housing (7). This cannula system offers the advantage that the catheter can be sealed at the tip and also may consist of several ducts without incurring any danger of leaks anywhere.

20 Claims, 4 Drawing Sheets

FOREIGN PATENT DOCUMENTS

| | | |
|---|---|---|
| EP | 0 381 062 | 8/1990 |
| EP | 0381062 | 8/1990 |
| EP | 0 401 179 | 12/1990 |
| EP | 0401179 | 12/1990 |
| EP | 0 567 321 | 10/1993 |
| EP | 0 599 564 | 6/1994 |
| EP | 0 646 386 | 4/1995 |
| EP | 0 719 565 | 12/1995 |
| FR | 2 655 548 | 6/1992 |
| FR | 2655548 | 6/1992 |
| GB | 2 030 454 | 4/1980 |
| GB | 2030454 | 4/1980 |
| WO | WO 95/20991 | 8/1995 |
| WO | WO 95/33002 | 12/1995 |
| WO | WO 96/25088 | 8/1996 |

* cited by examiner

CANNULA SYSTEM

RELATED APPLICATIONS

This is a continuation of application Ser. No. 09/446,066, filed Dec. 17, 1999 now U.S. Pat. No. 6,537,253 which is a 371 of PCT/EP98/03620, filed Jun. 16, 1998, which claims the priority benefit of German Application No. 197 25 680.5, filed Jun. 18, 1997.

The invention relates to a cannula system of the species defined in the preamble of claim 1 and used to insert a catheter into biological tissue or the like.

A cannula system is known from the European patent document A2 0,567,321 with which to insert a catheter into biological tissue and which comprises a steel cannula with a sharp front tip and a rear end where the cannula is affixed to a plastic fitting. Moreover the known cannula system comprises a plastic housing having a front aperture at its front end and a rear aperture at its rear end as seen in the direction of piercing. The fitting is held against the housing between an advanced position wherein the front end of the cannula axially projects beyond the housing, and a retracted position wherein the cannula is received in this housing and is displaceable in the axial cannular direction.

The known cannula system is used with a thin tube fitted with projection enclosing the cannula and allowing detachably connecting the tube to the housing of the cannula system.

In order to introduce a catheter into biological tissue, for instance the body of a patient using the cannula system, the cannula will be in its advanced position wherein the sharp tip projects beyond the housing and the front end of the tube in the direction of piercing, whereby it is possible then to insert the cannula into the skin of the patient and to insert the thin tube into the patient's body through the puncture.

After tube insertion, the user moves the fitting together with the cannula into the retracted position wherein the cannula is received in the housing and separates the housing from the tube. The sole purpose of moving the cannula into its retracted position is to prevent contact with the sharp cannula tip and hence any consequent injury and infections.

Infusion may be immediately carried out through the tube remaining in the patient's body or a flexible catheter may be inserted into the patient's body to infuse liquids into this body or to remove them from it.

One drawback of the known cannula system is that following tube insertion, the cannula system must be detached from the tube before a flexible feed hose can be attached to the tube. This feature entails further operational steps making handling more complex.

The PCT document US95/05,672 discloses a cannula system of the cited kind wherein the catheter is firmly affixed to the front end of the housing at which it terminates. In the retracted position of the slider, the cannula remains by its front end in the catheter and in this manner sets up fluid communication between the catheter and the hollow inside of the slider, this slider being fitted at its rear end with a hose adapter.

This known cannula system incurs the drawback of mandatorily requiring open-tip catheters and precludes closed-tip catheters and multi-duct catheters. Furthermore the system entails a large dead space and raises sealing difficulties.

The WO 95/20,991 patent document discloses a system for using micro-dialysis probes wherein the microdialysis probe first is seated in a cannula fitted with a longitudinal slot and this sub-assembly then is made to pierce the tissue. Once the microdialysis catheter is present in the tissue, the cannula is withdrawn and is separated through the slot from the fluid duct of the microdialysis catheter.

The patent document WO 96/25,088 discloses a device for using sensors which also requires a slitted needle which, subsequent to sensor application, can be separated form the sensor.

Because of the slitted cannula, both known systems entail complex manufacture and impractical operation.

The objective of the invention is to create a cannula system of the above cited kind which shall be suitable for closed-tip catheters and for multi-duct catheters, for instance for microdialysis catheters known from the German patent document A1 197 14 572 or German patent 33 41 170, and which shall be fully sealed.

The basic concept of the disclosure of the present invention is to guide the catheter through the slider and the housing as far as the rear housing end and to affix the catheter in a direction opposite the direction of puncturing, where the catheter can be directly connected to hoses. The catheter continues in especially advantageous manner beyond the rear housing end. Sealing is assured everywhere.

The catheter being affixed to the housing and/or the slider only in the direction opposite that of puncturing, it cannot be accidentally pulled rearward out of the housing, while at the same time it is possible to advance it in the direction of puncturing after such piercing arbitrarily far beyond the cannula tip. When the catheter is affixed to tie slider in the direction of puncturing, the cannula may be left prior to use in its retracted position wherein its tip is protected. The slider will be advanced prior to use and the catheter will be driven along.

However the catheter also may be wholly rigidly joined to the rear housing end, in which case it runs as far as the cannula tip when this cannula is in its advanced position.

While it is basically possible to keep the slider manually in position relative to the housing as the cannula is inserted, an appropriate embodiment of the invention makes use of locking means to lock the slider to the housing at least in the advanced slider position. Piercing may then be implemented solely by holding the housing. Thereafter unlocking, ie disengagement may be implemented and the slider may be retracted. For that purpose one embodiment of the invention provides means for manually retracting the cannula. Advantageously the housing comprises a slot running in the direction of displacement of the cannula and crossed by a radial protrusion of the slider. The slider can forced back by means of the said externally accessible protrusion.

In one embodiment of the invention, the slider comprises a two-arm lever pivoting about an axis transversely to its sliding direction, the front lever arm in the front limit position of the slider engaging from behind an edge at the front end of the housing and this lever being disengaged, that is unlocked, by pressing on the front lever arm. Accordingly the two-arm lever is an actuator both to disengage and lock and to displace the slider.

A spring is provided in an especially appropriate embodiment of the invention to load the slider in the direction of its rear limit position, the slider being kept in its front limit position by an externally disengageable catch. In this embodiment the spring implements the return motion of the slider and cannula, thus facilitating handling.

When using a spring, the catch appropriately comprises a hook which is connected to the slider and which in the front limit position of the slider engages behind an edge at the front end of the housing and which is yielding in the disengaging direction. This basic design of the catch allows a further development in which the hook is fitted with a protrusion projecting beyond the front housing end in such manner that upon the cannula puncturing by the cannula, the protrusion hits the tissue surface and unlocks the hook. In this embodiment cannula retraction practically is automatic and no particular attention need be paid to disengagement and retraction.

The disengaging means may be designed in a number of ways and the minimum distance between an obstacle and that housing which when reached shall cause the disengaging means to unlock can be selected within wide limits. In an appropriate further development of the invention comprising the locking means, these are fitted with a locking blade connected to the adapter and which in the locking position elastically enters a radial clearance inside the housing, the disengaging means comprising an axially displaceable disengaging element of which the front end projects radially beyond the front end of the housing and of which the rear end comprises a disengaging blade extending inside the housing and upon axial displacement of the disengaging element engages underneath the locking blade in the direction of the housing and moves out of the clearance. This design allows simple and economical manufacture and operates reliable.

In a further development of the above embodiment, the disengaging blade and the locking blade when at rest abut each other by means of bevels in such manner that upon axial displacement of the disengaging element the disengaging blade lifts the locking blade toward the housing. This design offers simple and economical manufacture.

In a further development of the embodiment comprising a disengaging blade and a locking blade, at least two disengaging blades and associated locking blades are present at diametrically opposite sites of the disengaging element or slider relative to the cannula. This embodiment prevents the disengaging element is prevented from being bent and the reliability of the disengaging means is improved.

In a further development of the embodiment comprising the disengaging element, its front end is substantially annular. In this manner reliable disengagement upon impact by the disengaging element on an obstacle is assured regardless of the angular position of the housing about the cannula axis.

In another embodiment of the invention, the spring is helical, in particular it is a compression spring coaxial with the cannula, and is mounted between the housing and the adapter. This embodiment is particular simple and economical in manufacture. By appropriately dimensioning the compression spring, the force acting on the slider toward the retracted position after disengagement will be selectable.

Another embodiment comprises retention means to hold the housing against a body surface, for instance the skin of a human. In this embodiment, following inserting the cannula cannula and moving it into its retracted position, the cannula system is held for instance on the skin of a human in such manner that stressing the catheter by the weight of remnant cannula system on the catheter shall be prevented.

In a further development of the embodiment comprising retention means, these adapters are fitted on the housing outside using adhesive means, in particular an adhesive strip. In this embodiment the housing adheres to the skin and can be subsequently removed from it, for instance as the catheter is removed from the patient's body.

Appropriately the housing comprises a substantially flattened surface to rest on the body surface, for instance the skin of a human. In this design the housing rests in substantially two-dimensional manner on the skin and as a result pressure points or the like are precluded from the skin.

Lastly in another embodiment of the invention, the front aperture of the housing comprises a free inside width substantially corresponding to the outside diameter of the cannula. In this embodiment the cannula is laterally guided into its advanced position on one hand, whereby sideways slippage of the cannula is averted during puncturing. On the other hand when the cannula has been retracted, the catheter will be guided in the front aperture of the cannula system. This design averts damages that might arise when a flexible catheter is bent immediately behind the cannula tip and away from latter and thereby would rest by its outside surface against the cannula tip.

The invention is elucidated below by illustrative embodiments shown in the drawings.

FIG. 1 shows a partly sectional sideview of a first embodiment of the cannula system of the invention in its advanced position, FIG. 2 is a topview of FIG. 1, FIG. 3 corresponds to FIG. 1, however the cannula being in its retracted position, FIG. 4 is a topview of FIG. 3 on the cannula system of FIG. 3, FIG. 5 is an enlarged section V—V of FIG. 1, FIGS. 6–9 elucidate the use of the cannula system or FIGS. 1–5, FIG. 10 is a sideview of a second illustrative embodiment of the cannula system of the invention, the cannula being in its advanced position, FIG. 11 shows the cannula system of FIG. 10, with the cannula in its retracted position, FIG. 12 is a section A—A of FIG. 11, FIG. 13 is a sectional view B—B of FIG. 11, and FIG. 14 is a sectional view through FIG. 10 in the region of a circle K of FIG. 10, FIG. 15 is a section of a third embodiment of the invention with advanced cannula, and FIG. 16 corresponds to FIG. 15 but for a retracted cannula.

FIG. 1 shows a cannula system 1 to insert a flexible catheter designed as a microdialysis catheter 2 into biological tissue or the like and comprising a cannula 3 with a sharp front end 4 and a rear end 5 against which the cannula 3 is held by a bush-shaped plastic slider 6. Moreover the cannula system 1 comprises a plastic tubular housing 7 comprising a front aperture 8 in the region of its front end as seen in the direction of puncturing and a rear aperture 9 in the region of its rear end as seen in said direction, the catheter 2 being guided through said rear aperture 9 and being affixed within it to the housing 7. The slider 6 is held in displacement manner along the cannula's axis in the housing 7 between an advanced position shown in FIG. 1 wherein the front end 4 of the cannula 3 axially projects beyond the housing 7 and a retracted position wherein the cannula 3 is received in the housing 7.

The housing 7 comprises at its top side a slot 17 which is masked in FIG. 1 but shown in FIG. 2 running in the direction of displacement of the slider 6 and through which passes a radial protrusion 10 of said slider, a two-arm lever 11 being mounted to that end of said protrusion which is away from the slider 6. The lever 11 comprises a front arm 12 to which is affixed a detent beak 13 and a manually driven rear arm 14. When the slider 6 is in the advanced position, the detent beak 13 resiliently engages from behind the front end, as seen in the direction of puncturing, of the housing 7.

The catheter 2 is held by a stopper 16 in the rear aperture 9 of the housing 7 and runs inside this housing and through the transverse slot 15 into the inside of the cannula 3 as far as almost its front end 4.

FIG. 2 is a topview of the retracted position of the slider 6 of the cannula system 1 of FIG. 1. A transverse slot 15 is shown which can be engaged by the detent beak 13.

FIG. 3 shows the cannula system of FIGS. 1 and 2, however with the slider 6 retracted and the detent beak 13 engaged in the transverse slot 15. In this position the sharp front end 4 of the cannula 3 is within the housing 7 and therefore harmless. The catheter 3 projects through the front aperture 8 into the housing 7 and thereby is guided in a manner precluding relative motion of catheter 3 and the sharp front end 4 of the cannula 3 and also protecting the catheter 3 against damage.

FIG. 4 is a topview of the configuration of FIG. 3.

FIG. 5 shows a section V—V of FIG. 1 on an enlarged scale. It is clear that the housing 7 comprises the slot 17 which guides the slider 6 together with its radial protrusion 10. The catheter 2 comprises a duct separation, ie it is a two-duct catheter. However the cannula system 1 of the invention also may be used with other catheters.

The housing 7 comprises a substantially flat surface 18 at its lower side for the purpose of resting against a surface, especially the skin of a human. The front aperture 8 of the housing 7 is oval and comprises a free inside width larger than the outside diameter of the cannula 3. However the front aperture 8 also may be of such free inside width as to substantially match the outside diameter of the cannula 3, whereby the cannula 3 in its retracted position shall be snugly guided in the front aperture 8. In this manner the catheter 2 is precluded from being bent immediately behind the front end 4 of the cannula 3 when latter is in its retracted position and being damaged by this end of the cannula 3.

The drawing however does not show, and therefore discussion is presently required, that an adhesive strip is mounted on the outside of the housing 7 to the flat surface 18, said strip forming a fastener to retain the housing 7 on a surface, in particular the skin of a human.

The operation of the cannula system 1 of the invention will presently be discussed in relation to FIGS. 6 through 9 showing various insertion stages of the catheter 2 into the tissue of a human using the cannula system 1.

When inserting the cannula 1 into the patient's skin symbolized in FIG. 6 by a line 19, the cannula 3 will be in its advanced position wherein its front end 4 projects axially beyond the housing 7 and beyond the front end of the catheter 2 and wherein the slider 6 is locked by the detent beak 13 to the housing 7. To insert the cannula system 1, a user seizes the housing 7, with a finger 20 resting on said housing as shown in FIG. 6, while puncturing the skin 19 with the front end 4 of the cannula 3.

Thereupon the user guides the cannula 3 into the tissue to a desired depth as shown in FIG. 7. Next by his finger 20 he drives the rear arm 14 of the lever 11, whereby the detent beak 13 disengages from the front end of the housing 7 and the slider 6 together with the cannula 3 thereupon can be displaced in the direction of an arrow 21 towards its retracted position.

In FIG. 8 the slider 6 is in its retracted position wherein the cannula 3 is received in its entirety in the housing 7, thereby reliably preventing the front end 4 of the cannula 3 from injuring the patient or damaging the part of the catheter 2 present in the body of the patient. Once the slider 6 is in its retracted position, the user releases the lever 11 which then by its detent beak 13 enters the transverse slot 15 of the slot 17 and in this manner locks the slider 6 in its retracted position to the housing 7.

Thereupon a protective foil of the adhesive strip mounted on the flat surface 18 may be removed and the housing 7 together with its flat surface 18 can be deposited flat on the skin 19 as shown in FIG. 9.

Next, in the position shown in FIG. 9, liquid may be infused into, or removed from the tissue by means of the catheter 2.

Because the cannula system 1 upon insertion of the catheter 2 into the tissue remains on said catheter and may not be detached from it, the handling of the cannula system 1 is substantially simplified and requires less time.

FIG. 10 shows a second embodiment of the cannula system. Identical or corresponding components are denoted by the same references.

The second embodiment of the cannula system 1 shown in FIG. 10 differs from the first embodiment of FIGS. 1 through 9 in that the locking means to lock the slider 6 on the housing 7 differs in design in the manner elucidated below in relation to FIG. 14, and in that disengaging means are provided which disengage the locking means when the cannula 3 is in its advanced position and when the front end of the housing 7—as seen in the direction of puncturing—arrives in the vicinity of an obstacle such as the skin of a patient.

In FIG. 10 the slider 6 together with the cannula 3 is in its advanced position. The disengagement means comprise a disengaging element 22 which is displaceably mounted on the housing 7 and of which the front end 23 is annular and coaxial with the cannula 3, and of which the rear end extends by disengagement blades 24, 25—elucidated further below in relation to FIG. 13—inside the housing 7.

FIG. 11 shows the cannula system 1 of FIG. 9 with the slider 6 in its retracted position wherein the cannula 3 is received inside the housing 7.

Figure 1:
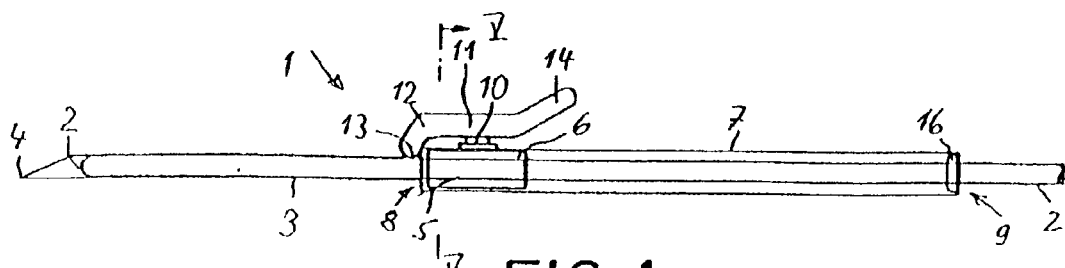
Figure 2:
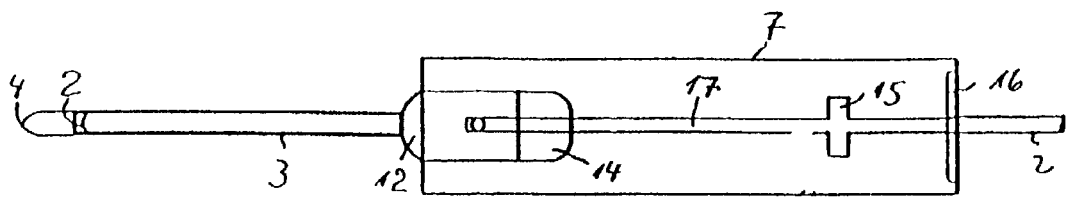
Figure 3:
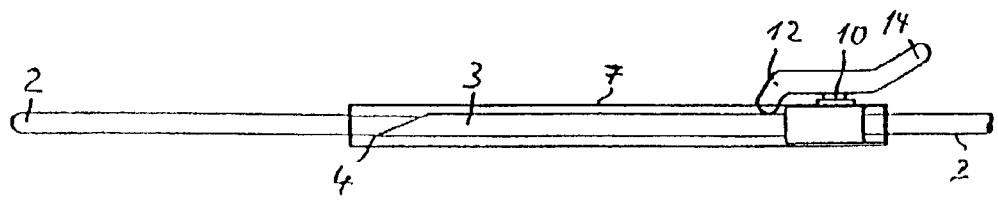
Figure 4:
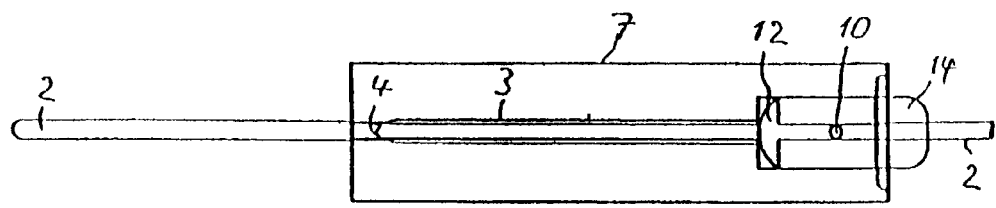
Figure 5:
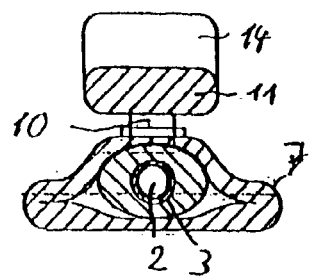
Figure 6:
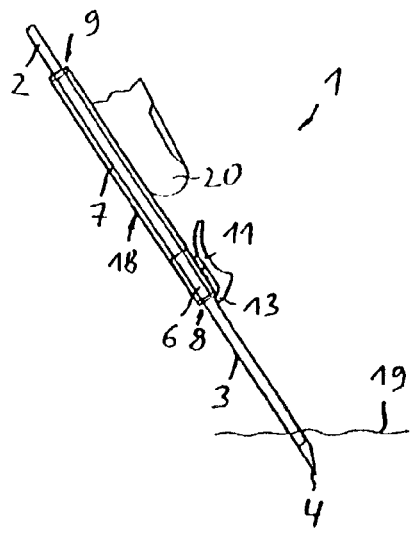
Figure 7:
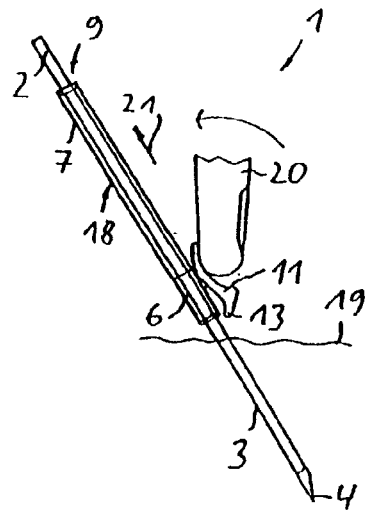
Figure 8:
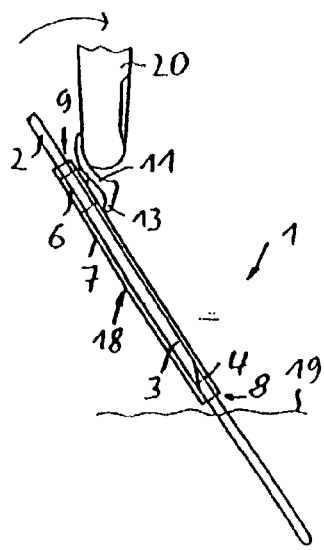
Figure 9:
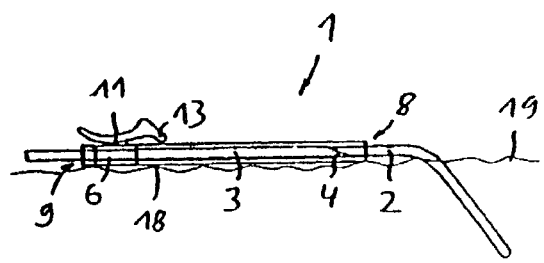
Figure 10:
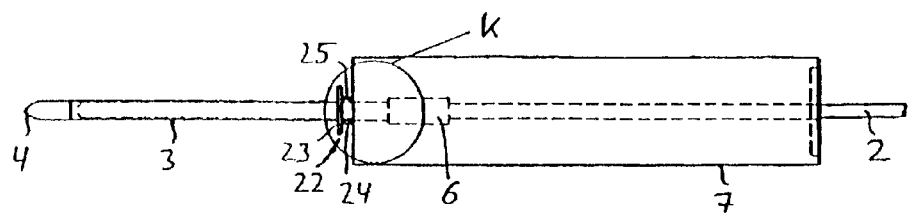
Figure 11:
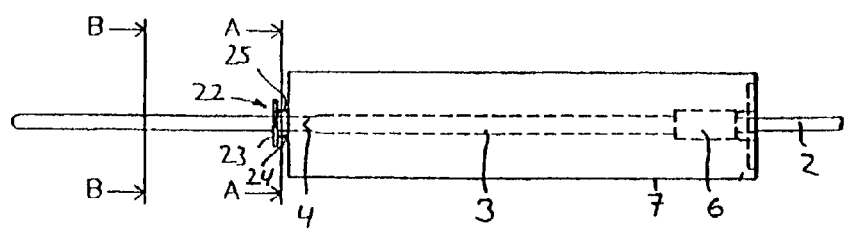
Figure 12:
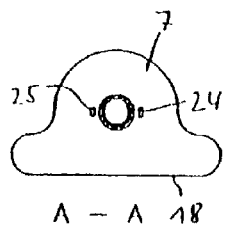
FIG. 12 shows a section A—A in FIG. 11 showing the disengaging blades 24, 25.
Figure 13:
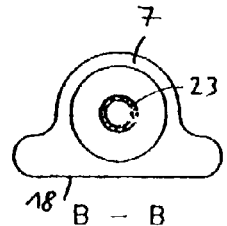
FIG. 13 shows a section B—B in FIG. 11 showing the annular end 23 of the disengaging element 22.
Figure 14:
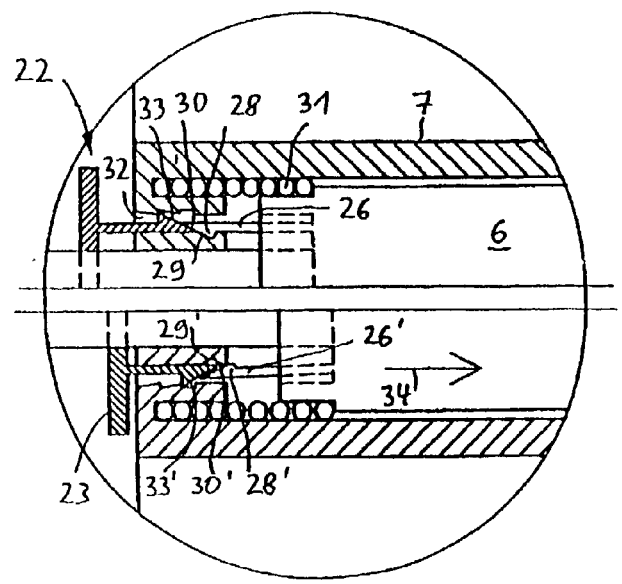
FIG. 14 shows a sectional elevation in the region of a circle K of FIG. 10.

The slider 6 is shown in its advanced position in the upper half of FIG. 14. In this embodiment the slider 6 is fitted with locking blades which, with respect to the cannula 3, are diametrically opposite, one locking blade 26 being shown in the upper half of FIG. 14 and another locking blade 26' being shown in the lower half of FIG. 14. By means of radially inward-pointing protrusions 28, 28', the locking blades 26, 26' resiliently enter radial clearances 29, 29'. The locking blades 26, 26' each comprise a bevel 30,30' at their end facing the disengaging element 22. A helical spring 31 is mounted between the axially inner end of the housing 7 and the slider 6 and biases the slider 6 when in its advanced, locked position in the direction opposite the direction of puncturing, that is in the direction of its retraction.

The disengaging blades 24, 25 of the disengaging element 22 run through apertures 32, 32' configured radially external to the front aperture 8 of the housing 7 and they comprise each a bevel 33, 33' at their end facing the disengaging blade 26, 26' which, by said bevel 33, 33' rest against the particular bevel 29, 29' of the locking blades 26, 26'.

The cannula system 1 of FIGS. 10 through 14 operates as follows:

For the piercing operation, the slider 6 will be in its advanced position to insert the cannula 3 so that the locking blades 26, 26' enter by means of their radial protrusions 28, 28' the radial clearances 29, 29' in the housing 7 and in this manner will lock the slider 6, which is spring-loaded, toward the retracted position against the housing 7. Illustratively the slider 6 already may be moved into the locked, advanced position when assembling the cannula system 1. However a drive element also may be used in the manner shown in FIGS. 1 through 9 to allow manually moving the slider 6.

As the front end—as seen in the direction of insertion—of the housing 7 comes into the vicinity of the patient's skin during the insertion operation of the cannula 3, the annular end 23 of the disengaging element 22 comes to rest against the skin and upon further insertion of said cannula said end is axially displaced toward the housing 7, as a result of which the disengaging blades 24, 25 by means of their bevels 30, 30' engage from below the bevels 33, 33' of the locking blades 26, 27 and lift them and thereby move them out of the radial clearances 29, 29' in the housing 7, so that the slider 6 is now disengaged and, under the bias of the helical spring 31, is returned in the direction of an arrow 34 into its retracted position.

Automatic disengagement of the locking means is implemented in this manner and undesired deep piercing by the cannula 3 is averted and handling of the cannula system 1 is made easier.

Figure 15:
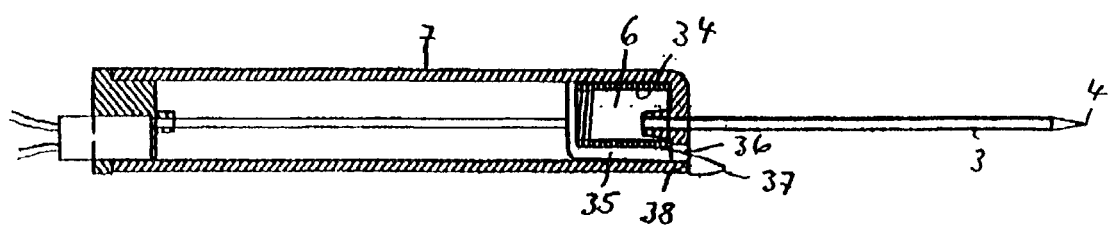

FIG. 15 shows a third embodiment of the invention. It differs from the embodiment of FIGS. 1 through 9 in that the slider 6 is spring-loaded opposite the piercing direction by a spring 34, that is toward the rear of the housing 7. An arm 35 is configured at the slider 6 and by its end projects through an aperture 36 into the front part of the housing 7, this arm furthermore comprising a hook 37 engaging from behind a front edge 38 of the housing 7 and in this manner keeping the slider 6 against the loading of the spring 34 in the position shown in FIG. 10. The arm 35 is resilient and accordingly the pressure of the hook may be disengaged from the front edge 38 and as a result the slider 6 can be forced to the rear by this spring 34, the slider 6 then carrying along the cannula 3 affixed to it and both assume the position shown in FIG. 16.

Figure 16:
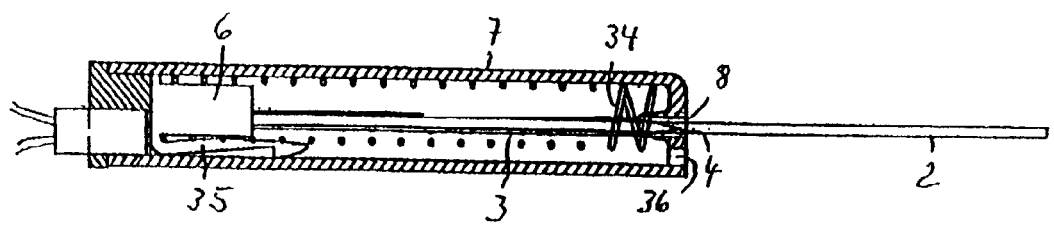

FIG. 16 shows that the length of the cannula 3 is such that the sharp front end 4 of the cannula 3 is situated within the front aperture 8 of the housing 7, as a result of which the catheter 2 is protected against damage from the sharp front end 4 of the cannula 3 because keeping the cannula 3 inside the housing 7 avoids relative motion of cannula 3 and catheter 2.

Basically the cannula system of FIGS. 15 and 16 is operated in the same manner as that of FIGS. 1 through 9 except that the manual return of the slider 6 is replaced by the force exerted by the spring 34. Disengagement of the hook 37 from the edge 38 is implemented in that following sufficient insertion of the cannula 3, the projecting hook 37 is pressed against the skin surface. Separate actuation of the hook 37 is therefore unnecessary.

The invention claimed is:

1. An catheter applicator system, said catheter applicator system comprising:
   a) a tubular housing, said tubular housing having a front end and a rear end;
   b) a slider, said slider is displaceable inside said tubular housing between a front limit position and a rear limit position;
   c) a cannula, said cannula having a front end and a rear end, said slider is rigidly joined to said cannula rear end, said cannula front end is fitted with a tip for piercing into biological tissue or the like, said cannula is received inside said tubular housing when said slider is in the rear limit position and at least partially projects from said housing when said slider is in the front limit position; and
   d) a catheter, said catheter having a front part adapted for insertion within an object and a fluid duct for conveying fluid at least one of to and from said catheter front part whereby upon insertion of said catheter front part into a biological tissue said cannula is caused to enclose at least a part of said catheter and be received inside said tubular housing.

2. An applicator system as in claim 1 and wherein said catheter is rigidly joined to said rear end of said housing and extends up to said front end of said cannula when said slider is in the front limit position and said cannula projects from said front end of said housing.

3. An applicator system as claimed in claim 1 and further including means for locking said slider against said housing at least in an advanced position of said slider.

4. An applicator system as claimed in claim 1 and further including means for manually retracting said cannula.

5. An applicator system as claimed in claim 4 and wherein said housing includes a slot which runs in the direction of displacement of said cannula and through which passes a radial protrusion operatively associated with said slider.

6. An applicator system as claimed in claim 4 and wherein said slider comprises a two-arm lever adapted to pivot about an axis transverse to its direction of displacement and of which a front arm, when in a detent position in the front limit position of the slider, engages from behind an edge at said front end of housing and which can be disengaged by pressing a rear arm.

7. An applicator system as claimed in claim 6 and wherein said slider and said two-arm lever are linked to each other by a protrusion projecting through a slot in said housing and running in the longitudinal direction of said housing.

8. An applicator system as claimed in claim 1 and further including a spring biasing said slider toward its rear limit position and by said slider being held in its front limit position by a detent member which can be disengaged from outside said housing.

9. An applicator system as claimed in claim 8 and wherein said detent member comprises a hook which is linked to said slider and which in the front limit position of said slider engages from behind an edge at said front end of said housing and which is resilient in the direction of disengagement.

10. An applicator system as claimed in claim 9 and wherein said hook projects beyond said front end of said housing in such manner that when said cannula is piercing said hook impacts the biological tissue surface and disengages said hook.

11. An applicator system as claimed in claim 4 and wherein said locking means comprises at least one locking blade which is linked with an adapter and which in the locking position by means of a radial protrusion resiliently enters a radial clearance inside said housing, and including means for disengaging comprising a disengaging element which is axially displaceable relative to said housing and of which a front end thereof projects axially beyond said front end of said housing and having a rear end comprises at least one disengaging blade which extends into the inside of said housing and upon axial displacement of said disengaging element engages the underside of said at least one locking blade to move said at least one locking blade out of the radial clearance.

12. An applicator system as claimed in claim 10 and wherein said at least one disengaging blade and said at least one locking blade when in the rest position rest against each other by means of bevels in such manner that upon axial displacement of said disengaging element said at least one disengaging blade lifts said at least one locking blade toward said housing.

13. An applicator system as claimed in claim 10 and wherein said at least one disengaging blade comprising at least two disengaging blades and said at least one locking blade comprising at least two locking blades, said at least two locking blades being situated relative to said cannula at diametrically opposite sites of said disengaging element.

14. An applicator system as claimed in claim 10 and wherein said front end of said disengaging element is substantially annular.

15. An applicator system as claimed in claim 8 and wherein said spring is a helical spring mounted between housing and said slider, and in particular a compression spring coaxial with said cannula.

16. An applicator system as claimed in claim 1 and further including means for retention of said housing on a surface.

17. An applicator system as claimed in claim 11 and wherein said retention means comprise an adhesive device mounted on the outside of said housing, said adhesive device is an adhesive strip.

18. An applicator system as claimed in claim 1 and wherein said housing comprises a substantially flat surface adapted to rest on the skin of a human.

19. An applicator system as claimed in claim 1 and wherein said front end of said housing having an aperture the inside width of which substantially matches the outside diameter of said cannula.

20. An applicator system as claimed in claim 1 and wherein said slider comprises a stop for said catheter when said slider is being advanced.

\* \* \* \* \*